(12) United States Patent
Vinokur et al.

(10) Patent No.: US 8,501,257 B2
(45) Date of Patent: Aug. 6, 2013

(54) POMEGRANATE SPROUTS, PREPARATIONS DERIVED THEREFROM AND COMPOSITIONS COMPRISING SAME

(75) Inventors: Yakov Vinokur, Rishon-LeZion (IL); Victor Rodov, Petach-Tikva (IL); Batia Horev, Or Yehuda (IL); Genady Goldman, Beer-Sheva (IL); Nehemia Aharoni, Mazkeret Batia (IL)

(73) Assignee: The State of Israel, Ministry of Agriculture & Rural Development, Agricultural Research Organization, (A.R.O.), Volcani Center, Beit-Dagan (IL)

( * ) Notice: Subject to any disclaimer, the term of this patent is extended or adjusted under 35 U.S.C. 154(b) by 171 days.

(21) Appl. No.: 12/670,881

(22) PCT Filed: Jul. 27, 2008

(86) PCT No.: PCT/IL2008/001033
§ 371 (c)(1),
(2), (4) Date: Jul. 1, 2010

(87) PCT Pub. No.: WO2009/016620
PCT Pub. Date: Feb. 5, 2009

(65) Prior Publication Data
US 2010/0278992 A1    Nov. 4, 2010

(51) Int. Cl.
*A23B 7/154*    (2006.01)
*A23L 3/28*    (2006.01)

(52) U.S. Cl.
USPC ............................ 426/321; 426/248; 426/541

(58) Field of Classification Search
USPC ......................................... 426/321, 248, 541
See application file for complete search history.

(56) References Cited

U.S. PATENT DOCUMENTS

| | | | |
|---|---|---|---|
| 5,725,895 | A | 3/1998 | Fahey et al. |
| 6,361,807 | B1 | 3/2002 | Aviram et al. |
| 6,800,292 | B1 | 10/2004 | Murad |
| 6,818,234 | B1 | 11/2004 | Nair et al. |
| 6,977,089 | B1 | 12/2005 | Aviram et al. |
| 2007/0148307 | A1 | 6/2007 | Sherwood et al. |

FOREIGN PATENT DOCUMENTS

| | | |
|---|---|---|
| JP | 2002-370996 | * 12/2002 |
| WO | WO 2006/127903 A1 | * 11/2006 |
| WO | WO 2009/016620 | 2/2009 |

OTHER PUBLICATIONS

Yoshimura, M., Watanabe, Y., Kasai, K., Yamakoshi, J., and Koga, T., "Inhibitory Effect of an Ellagic Acid-Rich Pomegranate Extract on Tyrosinase Activity and Ultraviolet-Induced Pigmentation," Biosci. Biotechnol. Biochem., 69 (12), 2368-2373 (2005).*

Seeram., N. P., Adams., L. S., Henning, S. M. Niu, Y., Zhang, Y., Nair, M., and Heber, D., "In vitro antiproliferative, apoptotic and antioxidant activities of punicalagin, ellagic acid and a total pomegranate tannin extract are enhanced in combination with other polyphenols as found in pomegranate juice," Journal of Nutritional Biochemistry, 16 (2.*

(Continued)

*Primary Examiner* — Humera Sheikh
*Assistant Examiner* — Jeffrey Mornhinweg

(57) ABSTRACT

A pomegranate sprout preparation is disclosed. Methods of producing pomegranate sprouts and pomegranate sprout preparation as well as food or feed products comprising same are also disclosed.

11 Claims, 6 Drawing Sheets
(5 of 6 Drawing Sheet(s) Filed in Color)

Juice 450 g
Including
Sugar 70 g
НАОХ 4700 μM TE

Whole fruit
1 kg

(56) References Cited

OTHER PUBLICATIONS

Lei, F., Xing, D., Xiang, L., Zhao, Y., Wang, W., Zhang, L., Du, L., "Pharmacokinetic study of ellagic acid in rat after oral administration of pomegranate leaf extract," Journal of Chromatography B, 796 (2003) 189-194.*

Naik, S. K., Pattnaik, S., Chand, P. K., "High frequency axillary shoot proliferation and plant regeneration from cotyledonary nodes of pomegranate (*Punica granatum* L.)" Scientia Horticulturae 85 (2000) 261-270.*

Response Dated Oct. 5, 2011 to Communication Pursuant to Rules 70(2) and 70a(2) EPC of Apr. 5, 2011 From the European Patent Office Re. Application No. 08789709.6.

International Preliminary Report on Patentability Dated Feb. 11, 2010 From the International Bureau of WIPO Re.: Application No. PCT/IL2008/001033.

International Search Report Dated Feb. 13, 2009 From the International Searching Authority Re.: Application No. PCT/IL08/01033.

Written Opinion Dated Feb. 13, 2009 From the International Searching Authority Re.: Application No. PCT/IL08/01033.

Aviram et al. "Pomegranate Juice Consumption Reduces Oxidatvie Stress, Atherogenic Modifications to LDL, and Platelet Aggregation: Studies in Humans and in Atherosclerotic Apoliprotein E-Deficient Mice", American Journal of Clinical Nutrition, 71: 1062-1076, 2000.

Ellis et al. "Punicacae", Handbook of Seed Technology for Genebanks: Compendium of Specific Germination Information and Test Recommendations, Interantional Board for Plant Genetic Resources, II(3): 3 P., May 1985.

Gil et al. "Antioxidant Activity of Pomegranate Juice and Its Relationship With Phenolic Composition and Processing", Journal of Agricriculture & Food Chemistry, 48(10): 4581-4589, 2000.

Hawkes et al. "Osmotic Concentration of Fruit Slices Prior to Freeze Dehydration", Journal of Food Processing and Preservation, 2(2): 265-284, Sep. 1978. p. 265, Abstract, § 1, p. 266, § 4.

Kasai et al. "Effects of Oral Administration of Ellagic-Rich Pomegranate Extract on Ultraviolet-Induced Pigmentation in the Human Skin", Journal of Nutritional Science and Vitaminology, 52(5): 383-388, 2006.

Lansky et al. "*Punica granatum* (Pomegranate) and Its Potential for Prevention and Treatment of Inflammation and Cancer", Journal of Ethnopharmacology, 109(2): 177-206, Jan. 19, 2007. p. 177, Abstract, p. 179, col. 1, § 1—col. 2, § 1, 4, p. 191, col. 1, § 1, col. 2, § 1, p. 192-193, Table 2, p. 195, col. 1, § 4, p. 196-197, Table 3.

Mars "Pomegranate Plant Material: Genetic Resources and Breeeding, A Review", CIHEAM—Options Mediterraneennes: Production, Processing and marketing of Pomegranate in the Mediterranean Region: Advances in Research and Technology, 42: 55-62, 2000. p. 59, § 5.

Singh et al. "Studies on the Antioxidant Activity of Pomegranate (*Punica granatum*) Peel and Seed Extracts Using In Vitro Models", Journal of Agriculture and Food Chemistry, 50(1): 81-86, Jan. 2, 2002.

Sproutpeople "The Basics of Sprouting", Sproutpeople, 5 P., 1993-2007. http://www.sproutpeople.com/grow/sprouting.html.

Tanaka et al. "Tannins and Related Compounds. XLI. Isolation and Characterization of Novel Ellagitannins, Punicorteins A, B, C and D, and Punigluconin From the Bark of *Punica granatum* L.", Chemical Pharmaceutical Bulletin, 34(2): 656-663, 1986.

Vinokur et al. "Method for Determining Total (Hydrophilic and Lipophilic) Radical-Scavenging Activity in the Same Sample of Fresh Produce", Proceeding of the 1st International Symposium on Natural Preservatives in Food Systems, Princeton, USA, Mar. 30-31, 2005, Acta Horticulturae, 709: 53-60, 2006.

Wang et al. "Bioactive Compounds From the Seeds of *Punica granatum* (Pomegranate)", Journal of Natural Products, 67(12): 2096-2098, Dec. 2004.

Xu et al. "Effects of Germination Conditions on Ascorbic Acid Level and Yield of Soybean Sprouts", Journal of the Science of Food and Agriculture, 85(6): 943-947, Apr. 30, 2005. p. 944, col. 1, § 2-5, col. 2, § 2, p. 945, col. 2, § 1.

Communication Pursuant to Rules 70(2) and 70a(2) EPC Dated Apr. 5, 2011 From the European Patent Office Re. Application No. 08789709.6.

Supplementary European Search Report and the European Search Opinion Dated Mar. 17, 2011 From the European Patent Office Re. Application No. 08789709.6.

Murkute et al. "Exudation and Browning in Tissue Culture of Pomegranate", Agricultural Science Digest, XP008133964, 23(1): 29-31, Mar. 2003.

Naik et al. "Ethylene Inhibitors, AgNO3 and Aminoethoxyvinylglycine Stimulates Direct Adentitious Shoot Organogenesis in Cotyledon Explants of a Fruit Tree, Pomegranate (*Punica granatum* L. Cv. Ganesh)", In Vitro Cellular & Developmental Biology Animal, XP008133927, 40: 61A, 2004.

Naik et al. "High Frequency Axillary Shoot Proliferation and Plant Regeneration From Cotyledonary Nodes of Pomegranate (*Punica grantaum* L.)", Scientia Horticulturae, XP002626321, 85: 261-270, 2000.

Naik et al. "Silver Nitrate and Aminoethoxyvinylglycine Promote In Vitro Adventitious Shoot Regeneration of Pomegranate (*Punica granatum* L.)", Database CAPLUS [Online], Chemical Abstracts Service, XP002626323, Retrieved From STN, Database Accession No. 2003:447005, Jun. 11, 2003. Abstract.

Sharon et al. "Plant Regeneration From Cotyledonary Node of *Punica granatum* L.", Database CAPLUS [Online], XP002626324, Retrieved From STN, Database Accession No. 2001:493467, Jul. 9, 2001. Abstract.

Office Action Dated Dec. 27, 2011 From the Israel Patent Office Re. Application No. 203502 and Its Translation Into English.

* cited by examiner

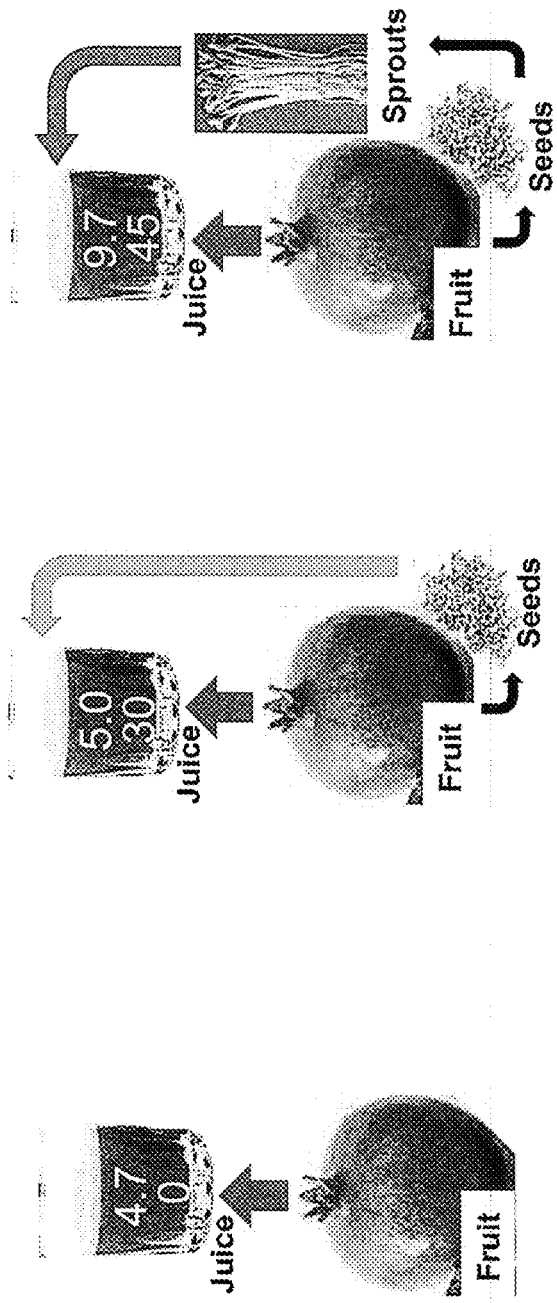

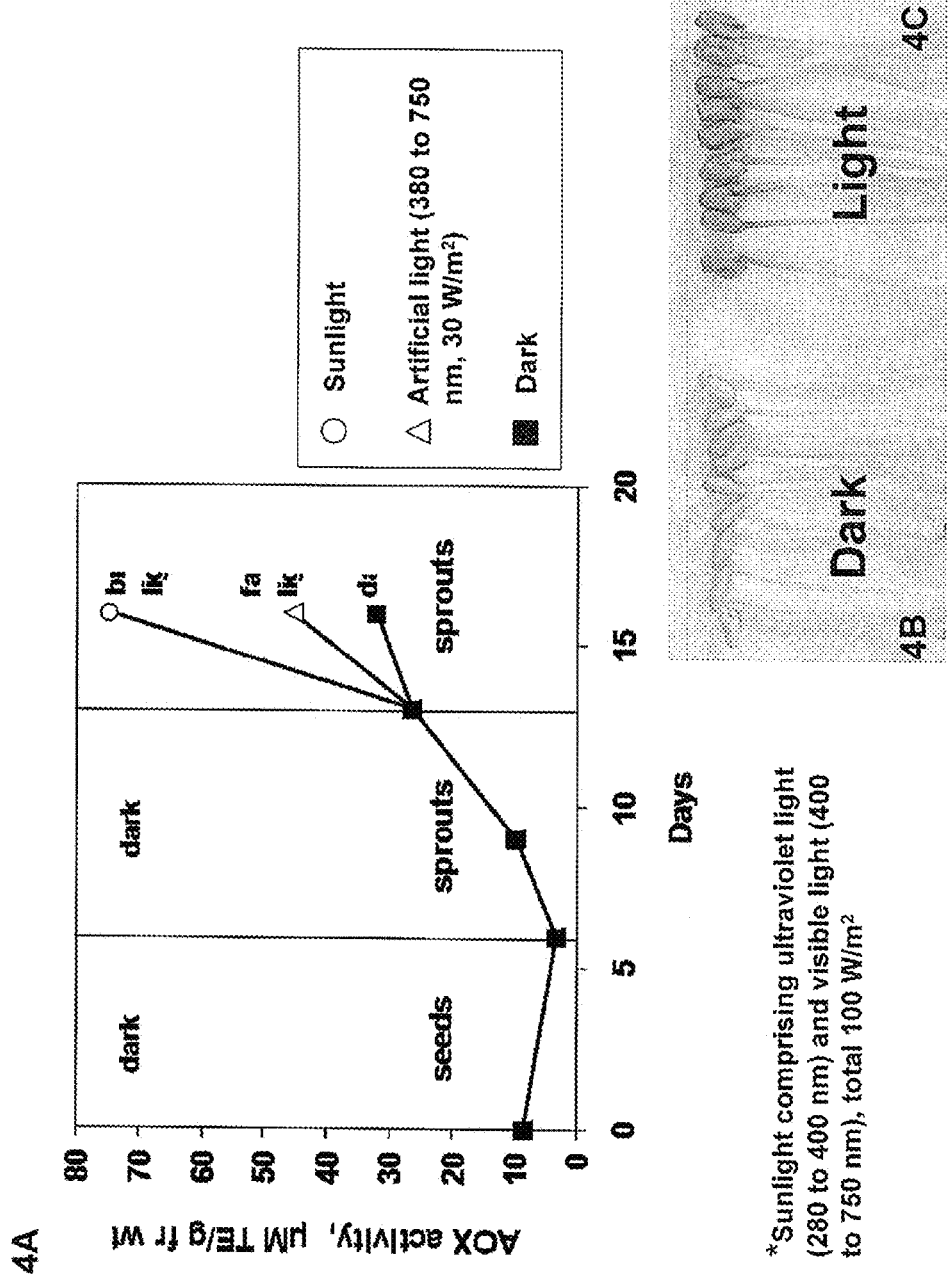
Figures 4A-C

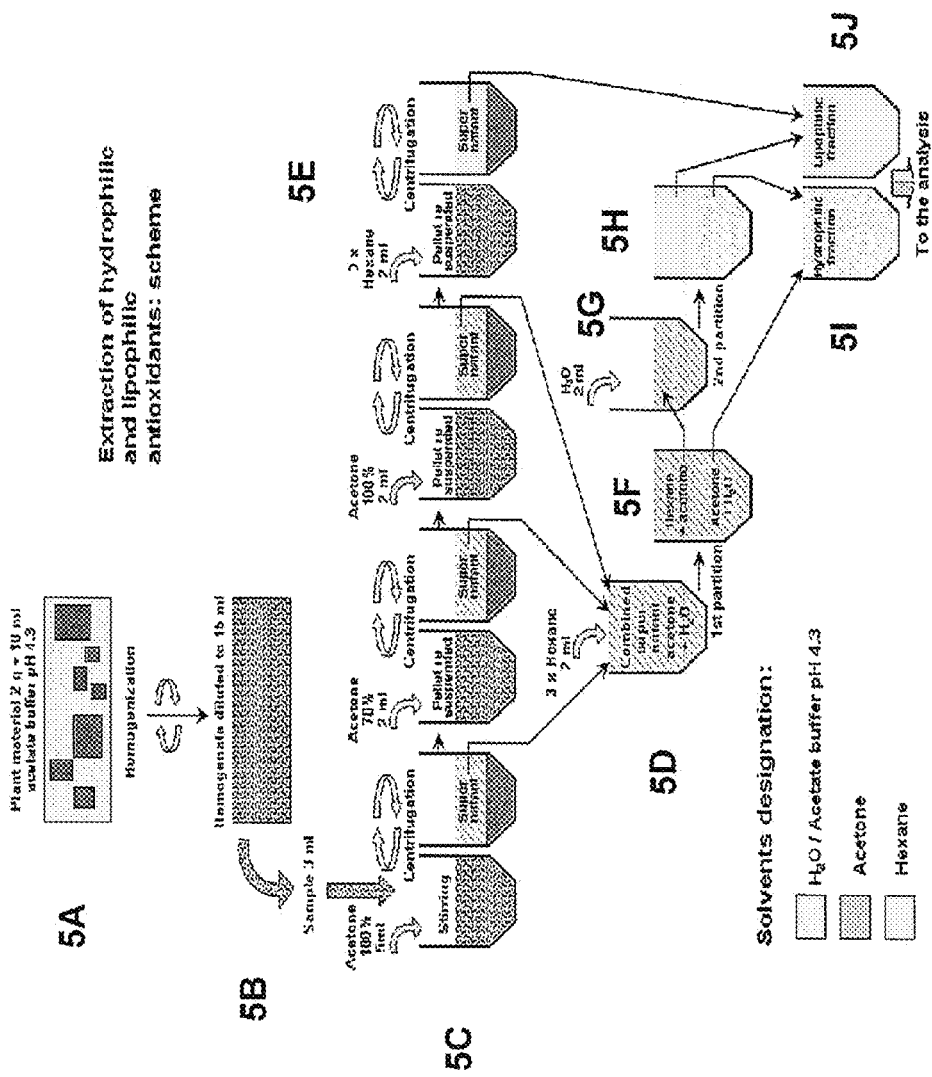
Figures 5A-J

POMEGRANATE SPROUTS, PREPARATIONS DERIVED THEREFROM AND COMPOSITIONS COMPRISING SAME

RELATED APPLICATIONS

This Application is a National Phase of PCT Patent Application No. PCT/IL2008/001033 having International filing date of Jul. 27, 2008, which claims the benefit of U.S. Provisional Patent Application No. 60/935,153 filed on Jul. 27, 2007. The contents of the above Applications are all incorporated herein by reference.

FIELD AND BACKGROUND OF THE INVENTION

The present invention, in some embodiments thereof, relates to pomegranate sprouts and preparations derived therefrom and, more particularly, but not exclusively, to the use of same.

Pomegranate (*Punica granatum L.*) is widely cultivated around the world and edible parts thereof have been used extensively in traditional medicines as well as in the food industry. For example, the Chinese have used the pomegranate as a traditional product in anti-bacterial, anti-inflammatory and homeostasis applications. In the functional food industry, the pomegranate is included in the novel category of superfruits, hence, it comprises an exceptional nutrient richness and antioxidant quality along with an appealing taste.

The edible part of pomegranate fruits (about 50% of total fruit weight) is composed of juicy seeds (arils) that comprise 80% juicy flesh and 20% true seeds. Fresh pomegranate juice contains sugars (i.e. fructose and glucose), organic acids (such as citric, malic, oxalic and tartaric acids), calcium, amino acids (mainly glutamic and aspartic acid), pectin, ascorbic acid and soluble polyphenols [mainly anthocyanins (such as cyanidin-3-glucoside, cyanidin-3,5-diglucoside and delphindin-3-glucoside), catechins and other flavonoids, gallic and ellagic acids and their derivatives]. In fact, juice obtained only from arils contains only trace amounts of ellagitannins, but juice obtained from whole fruits, including the peel, is enriched with ellagitannins [Gil et al., J Agric Food Chem (2000) 48: 4581-4589]. Pomegranate seeds are a rich source of lipids, proteins, crude fibers, pectin and sugars. Moreover, the pomegranate seeds contain the steroid estrogen estrone, the isoflavone phytoestrogens genistein and daidzein and the phytoestrogenic coumestrol [Kasai et al., J Nutr Sci Vitaminol (2006) 52(5):383-8; U.S. Pat. No. 6,361,807]. Pomegranate peels are a rich source of phenolics, however, they are very astringent.

Extracts from different parts of the pomegranate fruit including the juice [Gil et al., supra; Aviram et al., Am J Clin Nutr (2000) 71: 1062-1076], the seed [Wang et al., J Nat Prod (2004) 67: 2096-2098] and the peel [Singh et al., J Agric Food Chem (2002) 50: 81-86] have been previously shown to exhibit a strong anti-oxidant activity. Furthermore, pomegranate bark has been shown to be very rich in ellagitannins and gallotannins [Tanaka et al., Chem Pharm Bull (1986) 34: 656-663].

U.S. Pat. No. 6,977,089 discloses pomegranate extracts from whole pomegranate fruits (including inner and outer peels and seeds) for the treatment of atherosclerosis, artery related conditions and to decrease the incidence of stroke or heart attack in patients.

U.S. Pat. No. 6,800,292 discloses dermatological agents comprising a fruit tree extract (e.g. pomegranate) for treating dermatological disorders. The extract may be obtained from the fruit, the skin or rind of the fruit, the seeds, the bark, the leaves, the roots, or the stem.

U.S. Pat. No. 6,818,234 discloses food supplements that contain one or more fruit extracts (e.g. pomegranate) useful for pain relief and anti-inflammation. According to U.S. Pat. No. 6,818,234, the food supplements are extracted from the plants by a process which includes passing a solution (e.g. fruit juice) through an ultrafiltration membrane and then passing through a reverse osmosis membrane.

Additional related art is listed in http://ccne(dot)mofcom(dot)gov(dot)cn/206573/p1270843 (dot)html.

SUMMARY OF THE INVENTION

According to an aspect of some embodiments of the present invention there is provided a pomegranate sprout preparation.

According to an aspect of some embodiments of the present invention there is provided a method of producing a pomegranate sprout preparation, the method comprising: (a) providing pomegranate sprouts; and (b) processing the pomegranate sprouts, thereby producing the pomegranate sprout preparation.

According to an aspect of some embodiments of the present invention there is provided a method of producing pomegranate sprouts, the method comprising: (a) germinating pomegranate seeds in the dark until sprout emergence; (b) exposing the sprouts to light so as to obtain light-exposed sprouts; (c) incubating the light-exposed sprouts in the dark; and (d) harvesting the pomegranate sprouts, thereby producing the pomegranate sprouts.

According to some embodiments of the invention, (a) is effected for 6 to 13 days, wherein (b) is effected for 30 minute to 8 hours, wherein (c) is effected for 24 to 48 hours.

According to an aspect of some embodiments of the present invention there is provided a pomegranate sprout produced according to the method of claim 4.

According to an aspect of some embodiments of the present invention there is provided a pomegranate sprout comprising an anti-oxidative activity higher than 30 μM TE/g fresh weight.

According to an aspect of some embodiments of the present invention there is provided a food or feed product comprising the pomegranate preparation or pomegranate sprout of claim 1, 6 or 7.

According to some embodiments of the invention, the anti-oxidative activity of the preparation is higher than 30 μM TE/g fresh weight.

According to some embodiments of the invention, the providing is effected according to the method of claim 4.

According to some embodiments of the invention, the anti-oxidative activity is at least 50 μM TE/g fresh weight.

According to some embodiments of the invention, the anti-oxidative activity is at least 70 μM TE/g fresh weight.

According to some embodiments of the invention, the preparation or sprout comprises hydrophilic antioxidants.

According to some embodiments of the invention, the activity of the hydrophilic antioxidants comprises at least 70 μM TE/g fresh weight.

According to some embodiments of the invention, the hydrophilic antioxidants comprise Vitamin C.

According to some embodiments of the invention, the content of the Vitamin C comprises at least 0.3 mg/g fresh weight.

According to some embodiments of the invention, the hydrophilic antioxidants comprise phenolic compounds.

According to some embodiments of the invention, the phenolic compounds comprise gallic acid.

According to some embodiments of the invention, the content of the gallic acid is at least 16 mg/g dry weight.

According to some embodiments of the invention, the phenolic compounds comprise punicalagins.

According to some embodiments of the invention, the content of the punicalagins is at least 4 mg/g dry weight.

According to some embodiments of the invention, the phenolic compounds comprise flavonoids.

According to some embodiments of the invention, the content of the flavonoids is at least 19 mg/g dry weight.

According to some embodiments of the invention, the phenolic compounds comprise ellagic acid.

According to some embodiments of the invention, the content of the ellagic acid is at least 23 mg/g dry weight.

According to some embodiments of the invention, the preparation or sprout comprises lipophilic antioxidants.

According to some embodiments of the invention, an activity of the lipophilic antioxidants comprises at least 0.6 µM TE/g fresh weight.

According to some embodiments of the invention, the lipophilic antioxidants comprise Vitamin E.

According to some embodiments of the invention, the content of the Vitamin E comprises at least 0.40 mg/g fresh weight.

According to some embodiments of the invention, the lipophilic antioxidants comprise carotenoids.

According to some embodiments of the invention, the light comprises sunlight.

According to some embodiments of the invention, the light comprises ultraviolet light of a wavelength range of 280 to 400 nm.

According to some embodiments of the invention, the light comprises artificial light of a wavelength range of 380 to 750 nm of irradiance at least 30 W/m$^2$.

According to some embodiments of the invention, the preparation is in a granulated form.

According to some embodiments of the invention, the preparation is in a powder form.

According to some embodiments of the invention, the preparation is in a paste form.

According to some embodiments of the invention, the preparation is in a liquid form.

According to some embodiments of the invention, the processing is effected by homogenization.

According to some embodiments of the invention, the homogenization is effected in a presence of an organic acid.

According to some embodiments of the invention, the organic acid is a food grade organic acid.

According to some embodiments of the invention, the food grade organic acid is a citric acid.

According to some embodiments of the invention, the citric acid is at a concentration of 0.1% to 0.2%.

According to some embodiments of the invention, the processing is effected by drying.

According to some embodiments of the invention, the drying is effected by osmotic dehydration.

According to some embodiments of the invention, the drying is effected by freeze-drying.

According to some embodiments of the invention, the drying is effected by vacuum-drying.

According to some embodiments of the invention, the food or feed product is selected from the group consisting of a jelly, a sauce, a syrup, a relish, a wine, a cereal, a flake, a bar, a snack, a spread, a paste, a dip, a flour, a porridge, a beverage, an infusion, a decoction, a tincture, an extract, and a juice.

According to some embodiments of the invention, the food or feed product is selected from the group consisting of a dried sprout, a fresh sprout, a frozen sprout, a baked sprout, a stewed sprout, a fried sprout, an extruded sprout, a mashed sprout, a marinated sprout and a pickled sprout.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F are flow charts illustrating an exemplary process by which the food preparation of the present teachings are generated from pomegranate fruits. The process begins with 1 kg fresh pomegranate fruit (FIG. 1A) of which fresh juice can be extracted (FIG. 1B). About 50 g seeds can be obtained (FIG. 1C) from the juice extraction residue by separation from peels and waste (FIG. 1D). Next, these 50 g seeds are germinated (such as described in the materials and methods section hereinbelow) to generate about 150 g pomegranate sprouts (FIG. 1E). Food preparations are then produced from the pomegranate sprouts by, for example, freeze-drying or osmotic dehydration, or by homogenization of whole sprouts or only cotyledons (FIG. 1F). Of note, drying results in approximately 20-30 g dried material, osmotic dehydration results in approximately 30-35 g dried material, while homogenization results in approximately 150 g whole pomegranate derived homogenate or in approximately 50 g cotyledon derived homogenate. Importantly, the sprout preparations are obtained in addition to pomegranate juice obtained from the same fruits (depicted by + sign).

FIGS. 1G-I are flow charts comparing generation of pomegranate juice according to traditional methods (e.g., described in the Background section) compared to some embodiments of the present teachings. FIG. 1G depicts a traditional approach for producing pomegranate juice by pressing the juice from the whole fruit or from the arils. This pomegranate juice is rich in water-soluble antioxidants but has no lipophilic antioxidants (e.g. vitamin E); FIG. 1H depicts another traditional approach in which seed extract (seed oil) is added to the pomegranate juice. This addition enriches the juice with lipophilic antioxidants but has minor effect on total antioxidant activity and may add bitter taste to the juice; FIG. 1I depicts the methods according to some embodiments of the present teachings. Thus, adding pomegranate sprout preparations to the pomegranate juice enriches the juice with lipophilic antioxidants and doubles the total antioxidant activity.

Figure 2B:
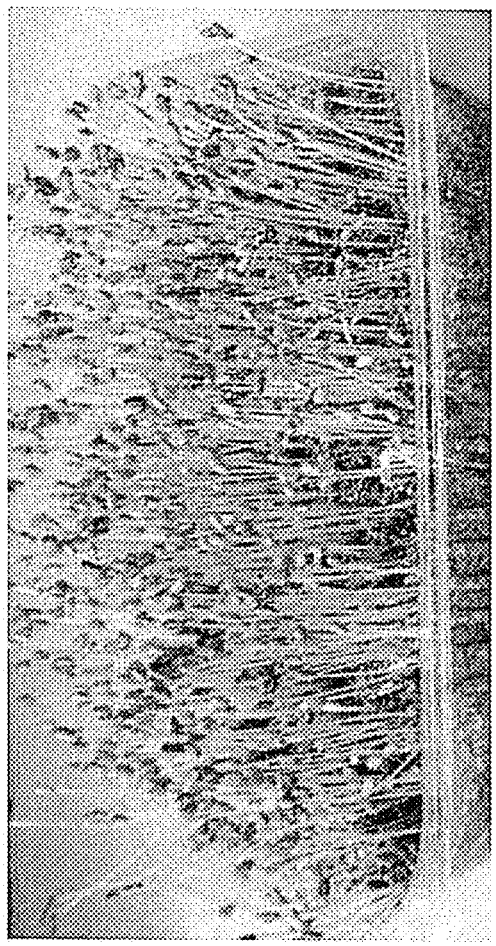
Figure 2A:
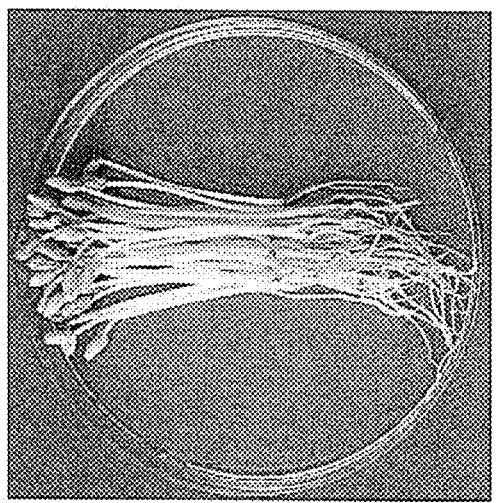

FIGS. 2A-B are images depicting the appearance of pomegranate sprouts. FIG. 2A depicts the pomegranate sprouts comprising cotyledons (seed leaves), hypocotyls (embryonic stems) and radicles (embryonic roots). FIG. 2B depicts growth of the pomegranate sprouts on a porous perlite substrate.

Figure 3:
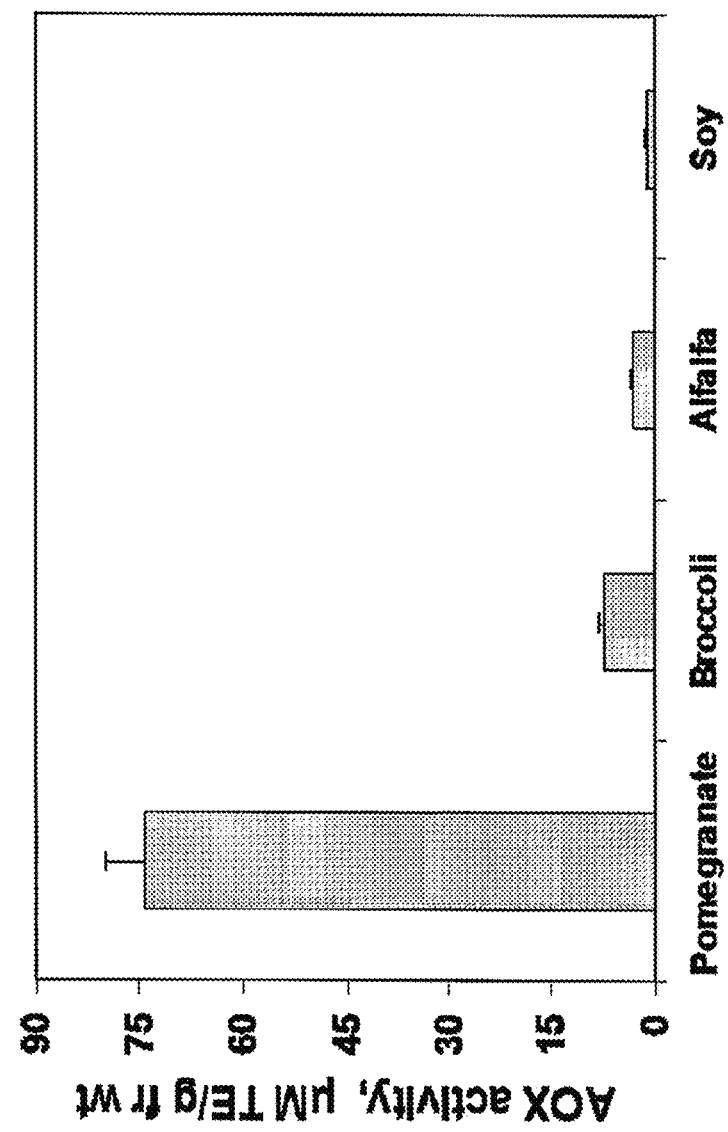

FIG. 3 is a bar graph depicting the antioxidant activity of pomegranate sprouts compared to other commercially grown sprouts derived from broccoli, alfalfa and soy. All sprouts were grown under the same growth conditions.

FIGS. 4A-C are figures depicting the effect of stage of development and illumination conditions on the pomegranate sprouts. FIG. 4A is a line graph depicting the antioxidant activity of pomegranate sprouts at different stages of development from seed to sprout. Furthermore, the graph illustrates the illumination effect on the antioxidant activity of the sprouts. FIGS. 4B-C are images depicting the appearance of pomegranate sprouts grown constantly in the dark (FIG. 4B) or with a 3 hour exposure to sunlight followed by additional 24 hours in the dark (FIG. 4C).

FIGS. 5A-J are flow charts schematically depicting the process used to extract lipophilic and hydrophilic antioxidants from pomegranate sprouts or pomegranate sprout preparations for measuring their activity. FIGS. 5A-B depict the fresh pomegranate sprouts homogenized in acetate buffer pH 4.3; FIG. 5C depict the extraction/dehydration of the homogenate with three successive portions of acetone, each step followed by centrifugation and collection of the supernatant; FIG. 5D depicts pooling of the acetone-water supernatant fractions from the three extractions; FIG. 5E depicts extraction of the dehydrated pellet three times with hexane and the supernatants were collected and pooled; FIG. 5F depicts extraction of the traces of lipophilic compounds from the pooled acetone-water extract by partitioning with hexane; FIGS. 5G-H depict the non-polar fraction obtained from this operation subjected to another partition with water in order to extract the traces of hydrophilic compounds; FIGS. 5I-J depict the two samples which were obtained, hydrophilic (water/acetone extract, FIG. 5I), and lipophilic (hexane extract, FIG. 5J).

DESCRIPTION OF SPECIFIC EMBODIMENTS OF THE INVENTION

The present invention, in some embodiments thereof, relates to pomegranate sprouts and preparations derived therefrom and, more particularly, but not exclusively, to the use of same.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have uncovered that pomegranate sprouts and preparations derived therefrom comprise an exceptionally high source of antioxidant activity without being astringent or bitter. This antioxidant activity comprises both hydrophilic and lipophilic antioxidants and is significantly higher than that of pomegranate fruit or seed, broccoli sprouts, alfalfa sprouts, soy sprouts, strawberry and avocado fruits. Thus, pomegranate sprouts and preparations derived therefrom may serve as food products, feed products and/or food additives comprising high nutritional values.

As is shown hereinbelow and in the Examples section which follows, the present inventors have shown that pomegranate sprouts of the present invention (FIGS. 2A-B), which are grown in a dark, light, dark cycle (FIG. 4A), comprise a total antioxidant activity of approximately 75 µM TE/g fresh weight. This antioxidant activity is ten times that of broccoli, soy and alfalfa sprouts (FIG. 3), 3-4 times that of strawberry fruit (Table 2, hereinbelow) and significantly higher than avocado fruit (Table 2, hereinbelow). The antioxidant activity of the pomegranate sprouts comprises hydrophilic components (e.g. Vitamin C, phenolic compounds) and lipophilic components (e.g. Vitamin E, carotenoids) and preparations obtained from these pomegranate sprouts provide for a rich source of antioxidants. The pomegranate sprout preparations were shown to comprise both hydrophilic antioxidants and lipophilic antioxidants, including Vitamins C and E, phenolic compounds, including gallic acid, ellagic acid, punicalagins, flavonoids (see Tables 1-3, hereinbelow, and FIGS. 1A-I). All these findings substantiate the use of pomegranate sprouts and preparations derived therefrom for use as food products, feed products and/or dietary supplements.

Thus, according to one aspect of the present invention there is provided a method of producing a pomegranate sprout preparation, the method comprising: providing pomegranate sprouts; and processing the pomegranate sprouts, thereby producing the pomegranate sprout preparation.

As used herein the term "pomegranate" is interchangeably used with *Punica granatum*.

The term "pomegranate sprout" as used herein refers to a developmental stage of a pomegranate plant ranging from a germinating seed to a plantlet that has at least two leaves, i.e. the cotyledons. The pomegranate sprout according to the present teachings comprises at least one pair of cotyledons (seed leaves), hypocotyls (embryonic stems) and radicles (embryonic roots) or a whole sprout.

The phrase "pomegranate sprout preparation" as used herein refers to a composition which is derived from a pomegranate sprout in which there is at least some breakage of plant membranes.

Pomegranate sprouts may be produced as follows. The method comprising: germinating pomegranate seeds in the dark until sprout emergence; exposing the sprouts to light so as to obtain light-exposed sprouts; incubating the light-exposed sprouts in the dark; and harvesting the pomegranate sprouts, thereby producing the pomegranate sprouts.

Pomegranate seeds are commercially available from, for example, http://www(dot)thompson-morgan(dot)com, http://seedrack(dot)com.

Alternatively, pomegranate seeds may be obtained from either the arils alone or from whole pomegranate fruit. Arils are obtained from pomegranates after separation of the peel, the arils are extracted to obtain juice, and the seeds are separated from the remaining flesh residue (as described in detail below, and in FIGS. 1A-D). If the seeds are to be obtained from whole pomegranate fruit, the whole fruit (including the peels) are typically first pressed to extract the juice and then the seeds are separated from all the pomegranate waste, including the remaining flesh residue.

Next, the seeds are cleaned by separation from residual juicy flesh matter and the seed coats are thinned using, for example, alkaline digestion (e.g. 20% alkaline solution such as NaOH or KOH) and mechanically separating the seeds from the partially digested flesh by abrasion against the rough surface. It is advisable that such a process will be carried out under cool conditions (e.g. in ice) in order to prevent seed heating above 40° C. (that may affect seed germination capacity). To neutralize and obtain seeds for germination, sulfuric acid may be used followed by a wash with water. The seeds may be dried in air at about 22-28° C. until no further change of weight is observed (weighing accuracy ±0.1 g per seed samples of 50 g), typically for 2 to 3 days. These seeds, ready for germination, may be stored at about 4° C. for up to 1-2 years.

Next, the seeds are sown (at a density of e.g. 4-5 seeds/cm$^2$) on a growth medium-soaked solid support (as described in detail hereinbelow), allowing air access, at a controlled temperature and humidity (as described in detail in Example 1 of the Examples section hereinbelow), in the dark until sprouts with cotyledons appear. Typically sprouts with cotyledons appear at a range of 6-21 days or 6-18 days or 6-13 days. In an exemplary embodiment, the range comprises 6-18 days.

A suitable growth medium for germinating pomegranate sprouts typically just contains water (e.g. tap water). Depending on the local quality of the tap-water further purification of the water may be required to demineralise the water and/or to remove chlorine, organic residues or other contaminants. In exemplary embodiments the water is free of microbial contaminants.

Typically the pomegranate sprouts are germinating on a non-nutritive solid support which provides air access, such as sponge, sponge-like material, agar, net, paper towel, blotting paper, Vermiculite, Perlite, etc., with water supplied. Furthermore, the non-nutritive solid support may comprise cellulose which may be applied in the form of pads, sheets or particles such as described for example in Dutch Patent No. 1001570.

Germination of the pomegranate sprouts is typically carried out at temperature ranging from 15-35° C., ranging from 20-30° C., or ranging from 22-27° C. Moreover, the pomegranate seeds are germinated at high humidity of at least 70%, at least 80%, at least 90%, or at least 100%. In an exemplary embodiment, the humidity is at least 90%. Germination may suitably be performed in a germination cell or room with controlled temperature and humidity as disclosed herein. Germination is carried out until the stage of a sprout with rolled cotyledons emerging from the seed coat; typically the seed coat drops from the sprout.

Following germination, the pomegranate sprouts are exposed to light so as to obtain light-exposed sprouts. Exemplary light nm range which may be employed includes 280 to 750 nm, which corresponds to sunlight, artificial light or ultraviolet light. For example, pomegranate sprouts may be placed in any location that is visible to sunlight (i.e. indoors or outdoors), at any hour of the day and under any weather condition. Likewise, pomegranate sprouts may be exposed to artificial light, including for example, faint indoor light or dim light, such as of wavelength ranging from 380 to 750 nm and of irradiance of at least 20 W/m$^2$, at least 30 W/m$^2$, at least 40 W/m$^2$, or at least 50 W/m$^2$. Furthermore, pomegranate sprouts may be exposed to ultraviolet light of wavelength ranging from 280 to 400 nm, ranging from 280-315 nm (i.e. UV-B) or 315-400 nm (i.e. UV-A). According to an exemplary embodiment, the sprouts are exposed to light at a temperature above about 10° C.

According to the present teachings, the pomegranate sprouts are exposed to light for a period of at least 20 minutes, at least 30 minutes, at least 1 hour, at least 2 hours, at least 3 hours, at least 4 hours, at least 5 hours, at least 6 hours, at least 7 hours, or at least 8 hours.

Following light exposure, the pomegranate sprouts are further incubated in the dark as to obtain pomegranate sprouts with maximal anti-oxidative activity (described in detail hereinbelow). Such incubation may be carried out for a period of at least 6 hours, at least 12 hours, at least 24 hours, at least 36 hours, or at least 48 hours.

Once the pomegranate sprouts have germinated and grown, the pomegranate sprouts are harvested. Harvesting the pomegranate sprouts is effected by separation from the substrate by collecting the whole sprouts (including cotyledons, hypocotyls and radicles). Alternatively, parts of the pomegranate sprouts may be detached (e.g. cotyledons, cotyledons plus hypocotyls and so forth). Harvesting the pomegranate sprouts may be effected using any method known in the art, including but not limited to, cutting, pulling, trimming or tearing. It will be appreciated that prior to harvesting of the pomegranate sprouts, the growth of the sprouts may be arrested, e.g. by cooling the pomegranate sprouts to about 4° C., for about 7 days. Furthermore, subsequent to harvesting of the pomegranate sprouts, the harvested matter may be maintained in a cooled environment prior to consumption or processing (as described in further detail hereinbelow).

As stated hereinabove, after the pomegranate sprouts are at hand, the sprouts may be used as is or may be further processed to produce preparations rich in antioxidants.

As used herein, the term "antioxidant" refers to a group of substances that are capable of inhibiting, preventing, reducing or ameliorating oxidative reactions. Exemplary antioxidants include vitamin C (ascorbic acid), vitamin E, vitamin A, B vitamins (e.g. vitamin $B_6$), flavonoids, selenium and carotenoids (e.g. beta-carotene).

As used herein, the phrase "anti-oxidative activity" refers to the act of neutralizing free radicals such as those found in a physiological environment.

The pomegranate sprout may be processed in its entirety, as described hereinabove. Alternatively, antioxidant-rich parts of the pomegranate sprout may be processed such as e.g., the cotyledons. Sprouts are typically processed by, for example, drying, homogenizing, crushing or extracting. Methods for processing sprouts are well known in the art (see for example U.S. Pat. No. 6,686,517, U.S. Pat. No. 5,725,895, WO 2004/043886, incorporated herein by reference) and may likewise be applied to the pomegranate sprouts of the invention.

Thus, according to the present teachings, the pomegranate sprouts may be dried. Any drying process known in the art may be used for drying the sprouts, as for example, osmotic dehydration, freeze drying, inert gas drying, air drying, or vacuum drying.

For example, the pomegranate sprouts may be air dried by placing them in a commercial air dryer at about 50° C. until the biomass contains less than 5% moisture by weight. Alternatively, freeze-drying may be used for sprouts that are sensitive to air-drying, for example due to oil rancidification. Sprouts may be freeze dried by placing them into a vacuum drier and dried frozen under a vacuum until the biomass contains less than about 5% moisture by weight.

The dried sprouts are stored for further processing as bulk solids or further processed into granulated form or powder form by grinding to a desired mesh sized powder.

Alternatively, the pomegranate sprouts may be homogenized. Any method known in the art may be employed to homogenize the pomegranate sprouts. For example, the sprouts may be homogenized as is (with no addition of liquid buffer) or supplemented with a homogenization buffer which may comprise, for example, protease inhibitors (see for example WO 2004/043886), or adding equal volumes of ethanol to form tincture. Any type of homogenizer may be used e.g., Brinkman Polytron Homogenizer (see for example U.S. Pat. No. 5,968,567).

Exemplary embodiments of the present teachings apply food grade organic acid, e.g. citric acid at a concentration of about 0.5% to 3% or about 1% to 2%, to achieve homogenization of the pomegranate sprouts. The present teachings also apply homogenization in acetate buffer pH 4.3 at a concentration of 50 mM. Other food grade organic acids, such as acetic, lactic, malic, phosphoric, hydrochloric, ascorbic may also be applied according to the present teachings.

The homogenized material obtained, typically in liquid or paste form, may further be used to extract and/or purify specific proteins and/or fractions, e.g. lipophilic or hydrophilic antioxidants, therefrom. Any method known in the art for extracting hydrophilic and lipophilic fractions may be applied. For example, a method employing a stepwise extractions using acetone and hexane and repeated partition of water-soluble and water-insoluble portions (described in detail in the Examples section hereinbelow) may be used. Likewise, any conventional conditions and techniques known in the art for extracting proteins may be applied (e.g., extraction, precipitation).

Extraction can also be carried out such as by using polar or non-polar organic solvents.

As mentioned hereinabove, and as depicted in detail in the Examples section which follows, pomegranate sprouts and preparations therefrom provide high nutritional values and are especially a rich source of anti-oxidative activity.

It will be appreciated that the pomegranate sprouts comprise an anti-oxidative activity at a level of at least 20, at least 30, at least 40, at least 50, at least 60, at least 70, or at least 80 µM Trolox equivalents (TE) per gram of fresh weight sprout material. Likewise, pomegranate sprout preparations comprise an anti-oxidative activity at a level of at least 20, at least 30, at least 40, at least 50, at least 60, at least 70, or at least 80 µM TE per gram of fresh weight sprout material.

According to specific embodiments of the present invention, the pomegranate sprouts and pomegranate sprout preparations comprise both hydrophilic and lipophilic antioxidants.

As used herein the term "hydrophilic antioxidants" refers to antioxidant compounds that have greater solubility in aqueous medium than in oil. Exemplary hydrophilic antioxidants include vitamin C and phenolic compounds, including gallic acid, ellagic acid, punicalagins and flavonoids.

As used herein the term "lipophilic antioxidants" refers to antioxidant compounds that have greater solubility in oil than in aqueous medium. Exemplary lipophilic antioxidants include the vitamin E family and carotenoids.

According to specific embodiments, the activity of the hydrophilic antioxidants in pomegranate sprouts or preparations comprise at least 30, at least 50, at least 70, at least 90, at least 110, at least 130, at least 150, or at least 200 µM TE per gram of fresh weight.

The hydrophilic antioxidants of the present invention comprise vitamin C (ascorbic acid). According to some embodiments of the present invention, the content of the vitamin C in pomegranate sprouts or preparations comprise at least 0.1, at least 0.2, at least 0.3, at least 0.4, or at least 0.5 mg per gram of fresh weight.

The hydrophilic antioxidants of the present invention further comprise phenolic compounds including gallic acid, ellagic acid, punicalagins A and B (ellagitannins) and flavonoids (free and bound).

According to some embodiments of the present invention, the content of the total phenolics in pomegranate sprouts or preparations comprise at least 7, at least 8, at least 9, at least 10, at least 20, at least 30, at least 40, or at least 60 gallic acid equivalents (GAE) per gram of fresh weight.

According to some embodiments of the present invention, the content of the gallic acid in pomegranate sprouts or preparations comprise at least 12, at least 14, at least 16, at least 18, or at least 20 mg per gram of dry weight.

According to some embodiments of the present invention, the content of the punicalagins in pomegranate sprouts or preparations comprise at least 1, at least 2, at least 3, at least 4, at least 5, or at least 6 mg per gram of dry weight.

According to some embodiments of the present invention, the content of the flavonoids in pomegranate sprouts or preparations comprise at least 15, at least 17, at least 19, at least 21, or at least 23 mg per gram of dry weight.

According to some embodiments of the present invention, the content of the ellagic acid in pomegranate sprouts or preparations comprise at least 17, at least 19, at least 21, at least 23, at least 25, or at least 27 mg per gram of dry weight.

According to an additional embodiment, the pomegranate sprouts and preparations comprise lipophilic antioxidants. The activity of the lipophilic antioxidants in pomegranate sprouts or preparations comprise at least 0.1, at least 0.2, at least 0.4, at least 0.6, at least 0.8, or at least 2.0 µM TE per gram of fresh weight.

The lipophilic antioxidants of the present invention comprise vitamin E. According to some embodiments of the present invention, the content of the vitamin E in pomegranate sprouts or preparations comprise at least 0.1, at least 0.2, at least 0.3, at least 0.4, or at least 0.5 mg per gram of fresh weight.

The lipophilic antioxidants of the present invention further comprise carotenoids.

According to the present teachings, but without being bond to theory, it will be appreciated that different levels and activities of antioxidants are present in different pomegranate sprout preparations. Thus, the highest levels of hydrophilic and lipophilic antioxidant activities are exhibited in dried preparations, especially freeze-dried preparations. Furthermore, cotyledon homogenates exhibit higher levels of hydrophilic and lipophilic antioxidant activities compared to whole sprout homogenates.

The anti-oxidative levels may be determined using any method known in the art, including TEAC (Trolox equivalent antioxidant capacity) as described in Example 1 hereinbelow, TRAP (total radical-trapping antioxidant parameter) and FRAP (ferric reducing-antioxidant power), see for example Pellegrini et al. J Nutr. (2003) 133: 2812-2819. These anti-oxidative levels relate to the total level of antioxidants present in pomegranate sprouts and preparations therefrom. Methods for determining anti-oxidative levels for hydrophilic and lipophilic compounds include TEAC and ORAC (oxygen radical absorbance capacity) method, see for example [Huang et al., J. Agric. Food Chem. (2002) 50:1815-1821].

It will be appreciated that the pomegranate sprouts and preparations further comprise oil, at least 3%, at least 5%, at least 7%, at least 9%, at least 10%, at least 15%, at least 20%, or at least 30% w/w, and further comprise nutritional fibers.

In a further aspect the invention, the pomegranate sprouts or preparations therefrom are comprised in a food or feed product (e.g., dry, liquid, paste). A food or feed product is any ingestible preparation containing the pomegranate sprouts, or parts thereof, of the instant invention, or preparations made from these sprouts. Thus, the sprouts or preparations are suitable for human (or animal) consumption, i.e. the sprouts or preparations are edible. Feed products of the present invention further include a beverage adapted for animal consumption.

For human consumption sprouts are typically free of soil. As described hereinabove, the pomegranate sprouts are typically not grown in soil, but on a solid support (e.g. sponge) supplemented with water. Thus, usually there is no need for the sprouts to be washed to remove non-edible soil. If the sprouts are grown in a particulate solid support, such as soil, Vermiculite, Perlite, or cellulose, washing may be required to achieve sprouts suitable for human consumption.

Such pomegranate sprouts may be packaged in suitable containers for shipping and marketing. Typically such containers are plastic boxes or jars which contain a wetted pad at the bottom and at times preservatives. For shipping, containers which limit light exposure while providing a mechanically protective barrier can be used. For marketing, containers which enable light penetration and provide a mechanically protective barrier may be used. The containers typically contain a plurality of such sprouts wherein the sprouts are preferably ready for consumption. The container may contain at least 1, at least 2, at least 3, at least 4, at least 5, at least 6, or at least 8, or at least 10 pomegranate sprouts per $cm^2$. Food products containing the pomegranate sprouts of the instant invention can be stored and shipped in diverse types of containers such as jars, bags and boxes, among many others.

It will be appreciated that the pomegranate sprouts may be consumed as is. These sprouts have an attractive taste and may be eaten directly or alternatively may be used to prepare fresh salads, drinks, or sandwiches. Alternatively, the sprouts may be dried, cooked, boiled, frozen, baked, stewed, fried, extruded, mashed, marinated, lyophilized or pickled prior to consumption.

Likewise, pomegranate sprout preparations may be consumed as is (e.g. as a spread) or alternatively may be added to existing or new food products. Exemplary food products comprising the pomegranate food products include, but are not limited to, breads, jellies, sauces, syrups, relishes, wines, teas, soups, cereals, flakes, bars, snacks, spreads, pastes, dips, flours, porridges, beverages, cocktails, infusions, decoctions, tinctures, extracts, chewing gums, chocolates, sweets, ice-creams and juices. Various methods are known to those skilled in the art for addition or incorporation of such products into foods, see for example http://www(dot)palvelu(dot)fi/evi/files/55_519_470.pdf.

It will be appreciated that the pomegranate sprouts of the present invention may be used directly as feed products or alternatively may be incorporated or mixed with feed products for consumption. Exemplary feed products comprising the pomegranate sprouts or preparations include, but are not limited to, grains, cereals, such as oats, e.g. black oats, barley, wheat, rye, sorghum, corn, vegetables, leguminous plants, especially soybeans, root vegetables and cabbage, or green forage, such as grass or hay.

As stated hereinabove, the pomegranate sprouts and preparations of the present invention are either tasteless or have a non distinctive taste and may be advantageously used as a taste inert supplement to dishes or recipes or at times be used to add a new flavor to recipes and dishes. Moreover, the pomegranate sprout preparations may be used as food additives to enrich the food with combined hydrophilic and lipophilic antioxidants.

The food or feed product of the present invention can also include additional additives such as, for example, sweeteners, flavorings, colors, preservatives, nutritive additives such as vitamins and minerals, condiments, amino acids (i.e. essential amino acids), emulsifiers, pH control agents such as acidulants, hydrocolloids, antifoams and release agents, flour improving or strengthening agents, raising or leavening agents, cohesive agents, gases and chelating agents, the utility and effects of which are well-known in the art. See Merriani-Webster's Collegiate Dictionary, 10th Edition, 1993.

Compositions comprising the extracts or compounds of the present invention can be further formulated for administration as dietary supplements using one or more consumable carriers. A "consumable carrier" is herein defined as any food, food ingredient, or food additive, or any excipient utilized for tabletting, encapsulation, or other formulation of an active agent for oral administration, whether for human or animal use. Specific additives are well known to those of skill and are listed in places such as the U.S. Pharmacopeia. For dietary supplements, the extract can be mixed according to methods routine in the art. Dietary supplements can be prepared in a variety of forms including, but not limited to, liquid, powder, or solid pill forms.

The pomegranate sprouts and preparations may be consumed for general health, but may be especially advantage to subjects susceptible to conditions associated with oxidative stress, such as artherosclerosis, diabetes, cancer, cardiovascular disease, liver disease and individuals at risk of developing neurodegenerative diseases such as Alzheimer's disease.

It is expected that during the life of a patent maturing from this application many relevant antioxidants will be developed and the scope of the term antioxidants is intended to include all such new technologies a priori.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Example 1

Pomegranate Sprouts and Preparations therefrom as an Exceptional Source of Antioxidants Materials and Experimental Procedures Methods of Obtaining Pomegranate Sprouts and Preparing Antioxidant Food Preparations Therefrom The following steps were carried out for producing antioxidant preparations from pomegranate sprouts:

Approximately 50 g of pomegranate seeds were obtained from 1 kg fresh pomegranate fruits.

Pomegranate seeds were cleaned by separation from residual juicy flesh matter using alkaline digestion. Namely, 10 ml of the 20% alkaline solution (NaOH or KOH) was added to approximately 70 g of the residue after juice squeezing, comprising flesh matter and the seeds. The mass was thoroughly mixed under cooled conditions (in a container kept on an ice bath) in order to prevent its heating above 40° C. that may affect seed germination capacity, and the seeds were mechanically separated from the partially digested flesh by abrasion against the rough surface. Sulfuric acid (5 N) was added to the mass for neutralization and the obtained seeds were washed in water. All together, the alkaline digestion and mechanical abrasion resulted in thinning of the seed coats.

The seeds were stored at about 4° C. until use, up to 1-2 years.

Seeds were germinated on a porous sponge-like substrate soaked with tap water in the dark at 22 to 27° C. until the stage of a sprout with rolled cotyledons emerging from the seed coat; typically the seed coat dropped from the sprout.

Next, sprouts were exposed to bright sunlight, faint room light or long-wave ultraviolet irradiation for a period of 3 to 5 hours.

Sprouts were incubated in the dark at 18 to 21° C. for an additional period of about 24-48 hours.

Harvesting the cotyledons (separately, together with the upper part of the hypocotyl, or included in the whole sprout to produce the antioxidant preparation material was carried out by separation from the substrate and/or detachment from the sprout with further employing one of the following methods:

Homogenization of the whole harvested matter with the addition of food-grade organic acid (citric acid) in concentration of 0.2% w/w to obtain a semi-liquid paste-like homogenate.

Drying was effected without a direct air contact with the harvested sprout tissue by vacuum-drying, freeze-drying, or osmotic dehydration to obtain a granulated dry matter which was further grounded into powder or left as granules.

Measuring Total Antioxidant Activity

TEAC (Trolox Equivalent Antioxidant Capacity) Assay

The method was carried out as was previously described [Vinokur, Y. and Rodov, V. (2006). Acta Horticulturae 709: 53-60] and was based on the ability of antioxidant molecules to quench the long-lived ABTS.$^+$, a blue-green chromophore with characteristic absorption at 734 nm, compared with that of Trolox, a water-soluble vitamin E analog. The addition of antioxidants to the preformed radical cation reduces it to ABTS, determining a decolorization. The reaction mixture for the generation of the ABTS.$^+$ radical cation contained 0.15 mM 2,2'-azino-bis-(3-ethylbenzothiazoline-6-sulphonic acid), diammonium salt (ABTS) and 0.075 mM of radical initiator 2,2'-azobis(2-amidinopropane)dihydrochloride (AAPH) in ethanol acidified with 0.1% sulfuric acid. The decolorization test was performed in plastic cuvettes by adding 10 µL of test sample to 1 mL of acidified ethanolic solution of ABTS$^+$ and measured as optical density at 734 nm after 15 min of incubation at room temperature in comparison with blank sample. The 1 mM solution of 6-hydroxy-2,5,7,8-tetramethylchroman-2-carboxylic acid (Trolox, a water-soluble derivative of the vitamin E) was used as a standard, and the radical-scavenging activity of samples was expressed as Trolox equivalent antioxidant capacity (TEAC) in µM of Trolox per g of fresh weight.

Measuring Lipophilic and Hydrophilic Antioxidant Activity

The procedure was carried out as was previously described [Vinokur, Y. and Rodov, V. (2006). Acta Horticulturae 709: 53-60]. In short, prior to the TEAC assay, hydrophilic and lipophilic fractions were extracted from pomegranate sprouts (as depicted in detail FIGS. 5A-J) without preliminary drying. The procedure was based on stepwise extraction of the sprouts with acetate buffer, acetone and hexane and repeated partition of water-soluble and water-insoluble portions. At first, the fresh pomegranate sprouts were homogenized in acetate buffer pH 4.3 and the homogenate extracted/dehydrated with three successive portions of acetone, each step followed by centrifugation and collection of the supernatant. The acetone-water supernatant fractions from the three extractions were pooled. After the acetone extraction, the dehydrated pellet was extracted three times with hexane and the supernatants were collected and pooled. The traces of lipophilic compounds were extracted from the pooled acetone-water extract by partitioning with hexane. The non-polar fraction obtained from this operation was subjected to another partition with water in order to extract the traces of hydrophilic compounds. After pooling the fractions, two samples were obtained, hydrophilic (water/acetone extract), and lipophilic (hexane extract). Until the partition stage, all the extraction steps for one sprout sample were performed in a single centrifuge test tube; the partition required two test tubes per sample.

Results

Using the teachings of the present invention, each kilogram of pomegranate fruit produced about 50 g of seeds that were used to generate about 150 g pomegranate sprouts which upon harvesting resulted in about 150 g homogenate food preparation or 20 to 30 gram dried food preparation (see FIGS. 1A-F). As is shown in Table 1 (below), the resultant preparations (homogenate or dried types) were enriched by up to 50-fold with hydrophilic antioxidants and phenolic compounds compared to the edible portion of fresh pomegranate fruit or to pomegranate seeds. These preparations also enriched the total anti-oxidative activity of pomegranate juice by at least 2-fold (see FIGS. 1G-I) and had significantly higher levels of hydrophilic antioxidants, lipophilic antioxidants and phenolic compounds compared to pomegranate juice.

TABLE 1

Content of hydrophilic and lipophilic antioxidants, pomegranate oil and total phenolic compounds in different pomegranate substances

| Object | Hydrophilic antioxidants µM TE*/g | Lipophilic antioxidants µM TE*/g | Oil, %*** w/w | Total phenolics mg GAE**/g |
|---|---|---|---|---|
| Fresh fruit, edible portion | 7.8 ± 0.3 | 0.12 ± 0.01 | 1.6 | 2.7 |
| Seeds, non-germinated (including seed coats) | 4.5 ± 0.6 | 1.5 ± 0.1 | 18.4 | 1.3 ± 0.2 |
| Pomegranate juice | 8-15 | trace | trace | ca. 3 |
| Food preparation - Cotyledon homogenate | 110.7 ± 1.8 | 0.6 ± 0.1 | 9.8 | 27.9 ± 4.2 |
| Food preparation - Whole sprout homogenate | 36.9 ± 0.6 | 0.2 ± 0.02 | 3.3 | 9.3 ± 1.4 |
| Food preparation after sprout osmotic dehydration | 135.4 ± 5.1 | 0.7 ± 0.1 | 18.6 | 32.2 |
| Food preparation after sprout freeze-drying | 233.4 ± 13.9 | 2.0 ± 0.1 | 29.7 | 63.4 ± 4.4 |

*TE—Trolox equivalents;
**GAE—gallic acid equivalents,
***hexane-extractable

The pomegranate sprouts (FIGS. 2A-B) generated according to the present teachings were also found to be highly enriched in antioxidant activity. The total antioxidant activity of fresh pomegranate sprouts was approximately 75 µM TE/g fresh fruit, which was 10-30 times that of broccoli, soy and alfalfa sprouts (FIG. 3). Moreover, the antioxidant activity of fresh pomegranate sprouts was 3-4 times that of strawberry fruit (Table 2, below), one of the rich antioxidant sources in the human diet. The total antioxidant activity of pomegranate sprouts was significantly higher then that of other nutritional products such as oat breakfast cereal (3.1 µM TE/g), wheat bran tablet (4.7 µM TE/g), wheatgrass tablet (9.0 µM TE/g), tomato sauce (1.4 µM TE/g), white sesame (hulled, 4.4 µM TE/g) and chickpea (2.3 µM TE/g). Taken together, pomegranate sprouts and preparations therefrom comprise a very high antioxidant activity.

TABLE 2

Content of hydrophilic and lipophilic antioxidants, vitamins C and E in pomegranate sprouts in comparison with strawberry and avocado fruits

| Object | Antioxidant activity, µM TE/g fresh weight | | Vitamin C, mg/100 g fresh weight | Vitamin E, mg/100 g fresh weight |
|---|---|---|---|---|
| | Hydrophilic | Lipophilic | | |
| Strawberry | 14 | <0.01 | 57 | trace |
| Avocado | 0.6 | 0.8 | 8 | 3.5 |
| Pomegranate sprouts | 74 | 0.6 to 1.1 | 39 | 47 |

Example 2

The Level of Antioxidants in Pomegranate Sprouts is Effected by the Developmental Stage and Illumination Materials and Experimental Procedures Methods of Obtaining Pomegranate Sprouts and Preparing Antioxidant Food Preparations Therefrom As described in Example 1, above.

Measuring Antioxidant Activity

As described in Example 1, above.

Results

The antioxidant activity of the pomegranate sprouts changes throughout the course of development from a seed to a sprout. The non-germinated pomegranate seeds comprised antioxidant activity of about 10 µM TE/g fresh weight (FIG. 4A). The level of antioxidants declined at an early stage of seed germination (rooting), but subsequently increased up to about 30 µM TE/g fresh weight, in particular with cotyledons expansion. Further accumulation of antioxidants slowed down if the sprout remained in the dark, but under illumination the antioxidant level continued to increase (FIG. 4A) and was followed by color change, from greenish-yellow to red after short light exposure followed by incubation in the dark (FIGS. 4B-C), or to green after continuous light exposure (data not shown).

The rate of antioxidant accumulation depended on light intensity (FIG. 4A). Five hours of sunlight illumination was sufficient to induce a major increase in antioxidant activity (approximately 75 µM TE/g fresh weight, FIG. 4A) in pomegranate sprouts. Similarly, the exposure to ultraviolet light of wavelength 365 nm (UV-A) or 312 nm (UV-B) for a period of time from 30 minutes to 3 hours (depending on the light intensity) enhanced the accumulation of antioxidants in pomegranate sprouts (data not shown). Exposure to faint room light also was sufficient to induce an increase in antioxidant activity (approximately 45 µM TE/g fresh weight, FIG. 4A).

The high antioxidant activity of pomegranate sprouts was predominantly due to the sprout cotyledons. The optimal developmental stage for use of the pomegranate sprout was a sprout with young cotyledons, however, the level of antioxidant activity did not decrease at more advanced stages of sprout development (formation of real leaves, data not shown). Yet, the at more advanced stages of development, the sprout became less suitable for processing due to the texture changes (tissues roughening related in particular to their lignification, data not shown).

Example 3

Active Ingredients in Pomegranate Sprouts and Extracts Therefrom

Materials and Experimental Procedures

Methods of Obtaining Pomegranate Sprouts and Preparing Antioxidant Food Preparations Therefrom As described in Example 1, above.

HPLC Analysis

HPLC instrument: Agilent 1100 HPLC with a photodiode-array detector (DAD) and column Phenomenex Synergi Hydro-RP 250×4.6 mm, 4 µm particle size. Flow rate 1.0 mL/min. Mobile phase A 1% formic acid in Milli-Q Water; mobile phase B acetonitrile. Mobile phase program: 5% B to 15% B for 18 min., then increasing to 65% B for 2 minutes; return to 5% B over 5 minutes and re-equilibration for 5 minutes. Temperature 30° C., injection volume 10 µL, UV detection at 260 nm.

Results

As described in detail in Table 2 (hereinabove), the antioxidants present in pomegranate sprouts were found to be predominantly hydrophilic antioxidants (HAOX). The hydrophilic compounds comprised ascorbic acid (vitamin C) and phenolic compounds (such as gallic acid, ellagic acid, flavonoid glycosides and punicalagins, see Table 3, below). HPLC analysis showed that a significant part of the phenolic fraction was represented by ellagic acid (approximately 23 mg/g dry weight, see Table 3 below). These phenolic compounds are well known for their high bioavailability and also comprise antimicrobial activity.

TABLE 3

Content of major groups of phenolic compounds in pomegranate cotyledons

| Group of compounds | Content, mg/g dry weight |
| --- | --- |
| Gallic acid and other monomer phenolic acids | 16.0 |
| Ellagic acid | 23.2 |
| Punicalagins A and B (ellagitannins) | 4.2 |
| Flavonoids (free and bound) | 19.6 |
| Total | 63.0 |

Besides hydrophilic antioxidants, the pomegranate sprouts were also found to be rich in lipophilic antioxidants (LAOX, see Table 2, hereinabove). The lipophilic antioxidant content in pomegranate sprouts was found to be close or higher to that of avocado fruit and was found to comprise vitamin E (tocopherols) and carotenoids.

Processing the pomegranate sprouts by either homogenization or by drying resulted in preparations being rich sources of antioxidants. The highest source of hydrophilic antioxidants, lipophilic antioxidants, pomegranate oil and phenols was recorded by the process of freeze-drying of the pomegranate sprouts (see Table 1, hereinabove). However, osmotic dehydration, homogenization (of the cotyledons alone or the whole sprout) also resulted in high levels of antioxidants and oil in comparison to the fresh pomegranate fruit or to the non-germinated seeds (see Table 1, hereinabove). Thus, pomegranate sprouts or cotyledons alone can serve for food preparations being rich in both natural hydrophilic and lipophilic antioxidants.

Taken together, the health value of pomegranate sprouts and preparations therefrom is related in particular to the presence of vitamin C (ascorbic acid), phenolic compounds (e.g., gallic acid, ellagic acid, punicalagins and flavonoids), vitamin E (tocopherols), carotenoids and nutritional fiber.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of producing pomegranate sprouts, wherein the sprouts comprise cotyledons, the method comprising:
   (a) germinating pomegranate seeds in the dark until cotyledon emergence wherein said germinating is effected for 6 to 13 days;
   (b) exposing said cotyledons to light for 30 minutes to eight hours so as to obtain light-exposed sprouts;
   (c) incubating said light-exposed sprouts in the dark for 24 to 48 hours; and
   (d) harvesting said pomegranate sprouts, thereby producing the pomegranate sprouts.

2. A pomegranate sprout produced according to the method of claim 1.

3. The pomegranate sprout of claim 2, comprising at least 0.3 mg of Vitamin C per g fresh weight.

4. The pomegranate sprout of claim 2, comprising at least 16 mg of gallic acid per g dry weight.

5. The pomegranate sprout of claim 2, comprising at least 4 mg punicalagin per g dry weight.

6. The pomegranate sprout of claim 2, comprising at least 19 mg flavonoids per g dry weight.

7. The pomegranate sprout of claim 2, comprising at least 23 mg ellagic acid per g dry weight.

8. The pomegranate sprout of claim 2, comprising at least 0.40 mg Vitamin E per g fresh weight.

9. The pomegranate sprout of claim 2, comprising at least 0.3 mg of Vitamin C per g fresh weight, at least 16 mg of gallic acid per g dry weight, at least 4 mg punicalagin per g dry weight, at least 19 mg flavonoids per g dry weight, at least 23 mg ellagic acid per g dry weight and at least 0.40 mg Vitamin E per g fresh weight.

10. A food or feed product comprising the pomegranate sprout of claim 2.

11. The food or feed product of claim 10, which is selected from the group consisting of a jelly, a sauce, a syrup, a relish, a wine, a cereal, a flake, a bar, a snack, a spread, a paste, a dip, a flour, a porridge, a beverage, an infusion, a decoction, a tincture, an extract, and a juice.

* * * * *

UNITED STATES PATENT AND TRADEMARK OFFICE
CERTIFICATE OF CORRECTION

| | |
|---|---|
| PATENT NO. | : 8,501,257 B2 |
| APPLICATION NO. | : 12/670881 |
| DATED | : August 6, 2013 |
| INVENTOR(S) | : Yakov Vinokur et al. |

Page 1 of 1

It is certified that error appears in the above-identified patent and that said Letters Patent is hereby corrected as shown below:

Priority Data:

On the title page, immediately after the

"Prior Publication Data" item [65], insert the following section and text:

-- Related U.S. Application Data

(60) Provisional application No. 60/935,153, filed on

July 27, 2007. --

Signed and Sealed this
Twentieth Day of May, 2014

Michelle K. Lee
*Deputy Director of the United States Patent and Trademark Office*